(12) United States Patent
Witelson et al.

(10) Patent No.: US 11,493,495 B2
(45) Date of Patent: Nov. 8, 2022

(54) SWIMMING POOL FLOATING MAINTENANCE SYSTEM

(71) Applicant: Maytronics Ltd., Kibutz Yizrael (IL)

(72) Inventors: Shay Witelson, Kibbutz Yizrael (IL); Yair Hadari, Kibbutz Hulata (IL)

(73) Assignee: MAYTRONICS LTD., Kibbutz Yizrael (IL)

( * ) Notice: Subject to any disclaimer, the term of this patent is extended or adjusted under 35 U.S.C. 154(b) by 885 days.

(21) Appl. No.: 16/278,882

(22) Filed: Feb. 19, 2019

(65) Prior Publication Data

US 2019/0257807 A1 Aug. 22, 2019

Related U.S. Application Data

(60) Provisional application No. 62/633,639, filed on Feb. 22, 2018.

(51) Int. Cl.
| | | |
|---|---|---|
| *G01N 33/18* | (2006.01) | |
| *E04H 4/14* | (2006.01) | |
| *G05D 1/02* | (2020.01) | |
| *E04H 4/12* | (2006.01) | |
| *B63B 35/00* | (2020.01) | |

(52) U.S. Cl.
CPC ......... *G01N 33/1886* (2013.01); *B63B 35/00* (2013.01); *E04H 4/1209* (2013.01); *E04H 4/14* (2013.01); *G01N 33/1826* (2013.01); *G05D 1/0206* (2013.01)

(58) Field of Classification Search
CPC ............ G01N 33/1886; G01N 33/1826; B63B 35/00; E04F 4/1209; E04H 4/14; G05D 1/0206
USPC .......................................................... 701/21
See application file for complete search history.

(56) References Cited

U.S. PATENT DOCUMENTS

| | | | | |
|---|---|---|---|---|
| 9,511,831 | B2 * | 12/2016 | Kimura .................. | B63G 8/001 |
| 9,612,230 | B2 * | 4/2017 | Kano ..................... | A61J 1/1475 |
| 11,087,895 | B2 * | 8/2021 | Cole ........................ | G05D 1/00 |
| 2015/0346726 | A1 * | 12/2015 | Davoodi ................ | B63G 8/001 |
| | | | | 701/21 |

* cited by examiner

*Primary Examiner* — Gertrude Arthur Jeanglaude
(74) *Attorney, Agent, or Firm* — Reches Patents

(57) ABSTRACT

A method for analyzing a fluid of a pool by a floating system. The method may include sensing, by a sensor of the floating system, at least one out of (a) a wind parameter related to a wind that impinges on the floating system and (b) a movement of the floating system; wherein the floating system further comprises a top portion comprises at least one float, a submerged portion that comprises comprises a fluid analysis instrument, a power source, a controller, and a propulsion unit; determining, by the controller, an impact of the wind on the floating system based on the at least one out of the wind parameter and the movement of the floating system; controlling, by the controller, a movement of the floating system based, at least in part, on the impact of the wind; and analyzing, by the fluid analysis instrument, at one or more analysis points, the fluid of the pool to provide one or more fluid analysis results.

20 Claims, 13 Drawing Sheets

SWIMMING POOL FLOATING MAINTENANCE SYSTEM

CROSS REFERENCE

This invention claims priority from U.S. provisional patent Ser. No. 62/633,639 filing date Feb. 22, 2018.

BACKGROUND OF THE INVENTION

"Swimming pool" or "pool" mean any spa or tank or any reservoir containing liquid.

Fluid treatment in general has the aim of maintaining fluid quality parameters on a continuous basis. This process is based on sampling, sensing, analyzing and appropriately responding to results of pool water analysis.

Preventive pool water analysis and subsequent measures has a major effect on the time and cost required to maintain hygienic water characteristics by dispensing economical and safe chemicals at the right time.

Preventive measures may include, for analysis and warning about hygiene level deviations, the use of pool maintenance systems that are available in the market.

The causes for water quality deteriorations of a pool may be related to water chemistry imbalance or to biological effects.

Chemical imbalance may be caused due to lack of water hygiene maintenance chemicals such as Chlorine, acid and the like (or too much of these).

Biological effects may be caused by the chemicals imbalance that bring about growths of algae, bacteria, fungi, viruses, microbes and the like.

Further, natural events may speed up deterioration a pool condition. Examples may be, an unusually high number of swimmers in a small domestic pool or, a sudden gush of wind that may suddenly fill a pool with debris such as leaves that may start to rot whereby both such examples may bring about rapid drop in chlorine levels.

A variety of such pool maintenance systems may be used.

There is a growing need to provide cost effective swimming pool fluid monitoring systems and methods.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE DRAWINGS

Figure 1:
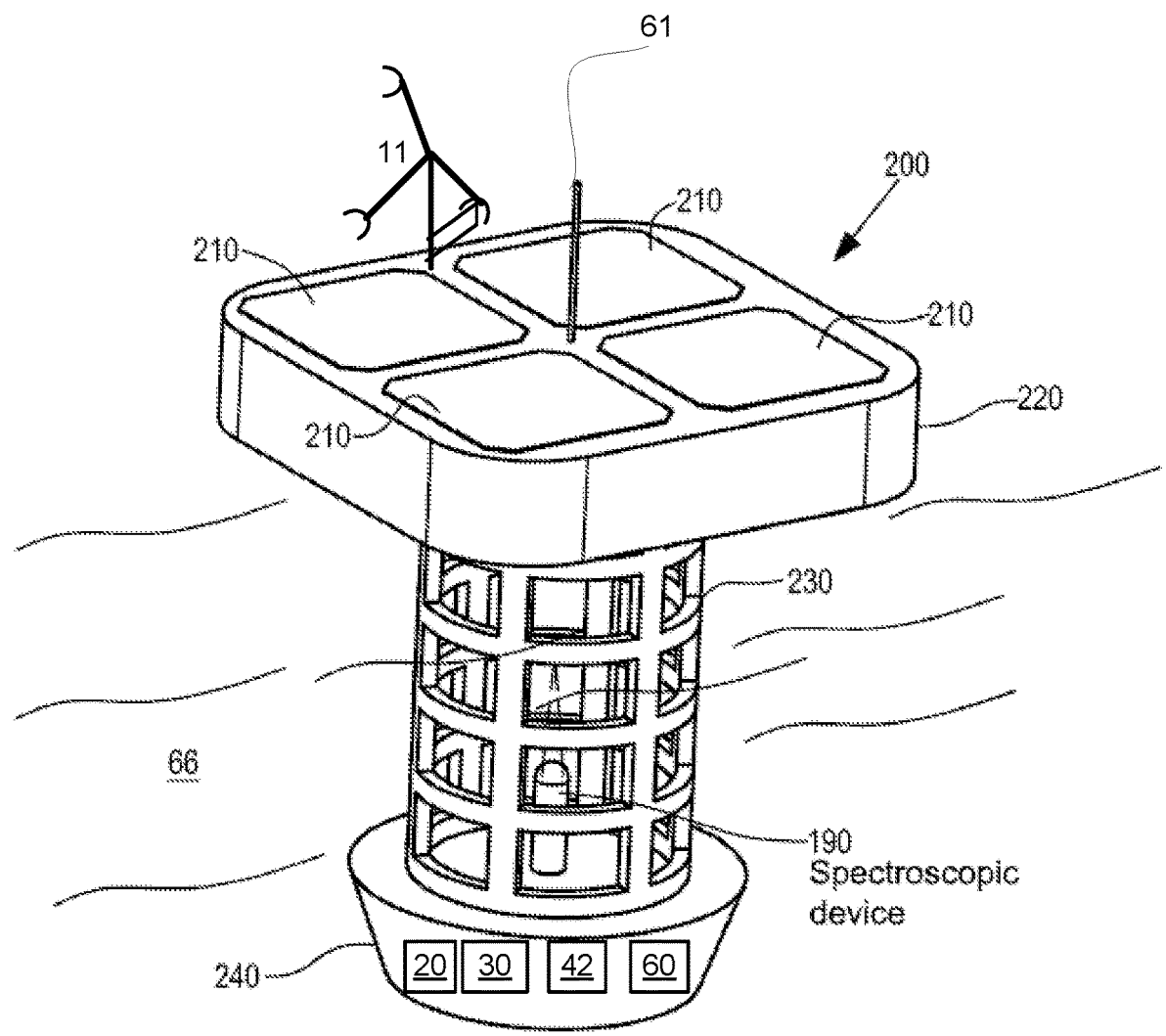
FIG. 1 is an examples of a floating system.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method.

Any reference in the specification to a system should be applied mutatis mutandis to a method that may be executed by the system.

According to an embodiment of the invention there may be provided a swimming pool maintenance system (also referred to as system).

The swimming pool maintenance system may be a floating system (or a "float") that may be at least partially submerged in the fluid of the pool when the pool may be at least partially filled with the fluid of the pool.

The floating system may be motorized to be able to travel on water surface and may include at least one out of (i) a propulsion system, (ii) navigation system, (iii) solar panels, (iv) rechargeable batteries, (v) inductive or wired battery recharging element, (vi) bumpers or bumper wheels, (vii) electronic control box, (viii) communication module, (ix) one or more sensors such as but not limited to accelerometer, inclinometer, acoustic sensor, camera, image sensor, stereoscopic camera, position sensor, anemometer, a controller, a compass, a gyroscope, a gyrocompass, a pressure sensor (such as a piezoelectric sensor).

It should be noted that the floating system may be remotely controlled. For example—another system may determine the location of the floating system and may control the movement of the floating control. Yet for another example—another system may determine the location of the floating system and may send location information to the floating system—and the floating system may determine how to propagate in the pool based on the location information.

The floating system may include a floating system and a ballasting mean and, solar panels, and a control unit, and a wireless communications pack.

FIGS. 1-7 illustrate various example of a floating system. In these figures the following numbers are used:

11—anemometer

Figure 2:
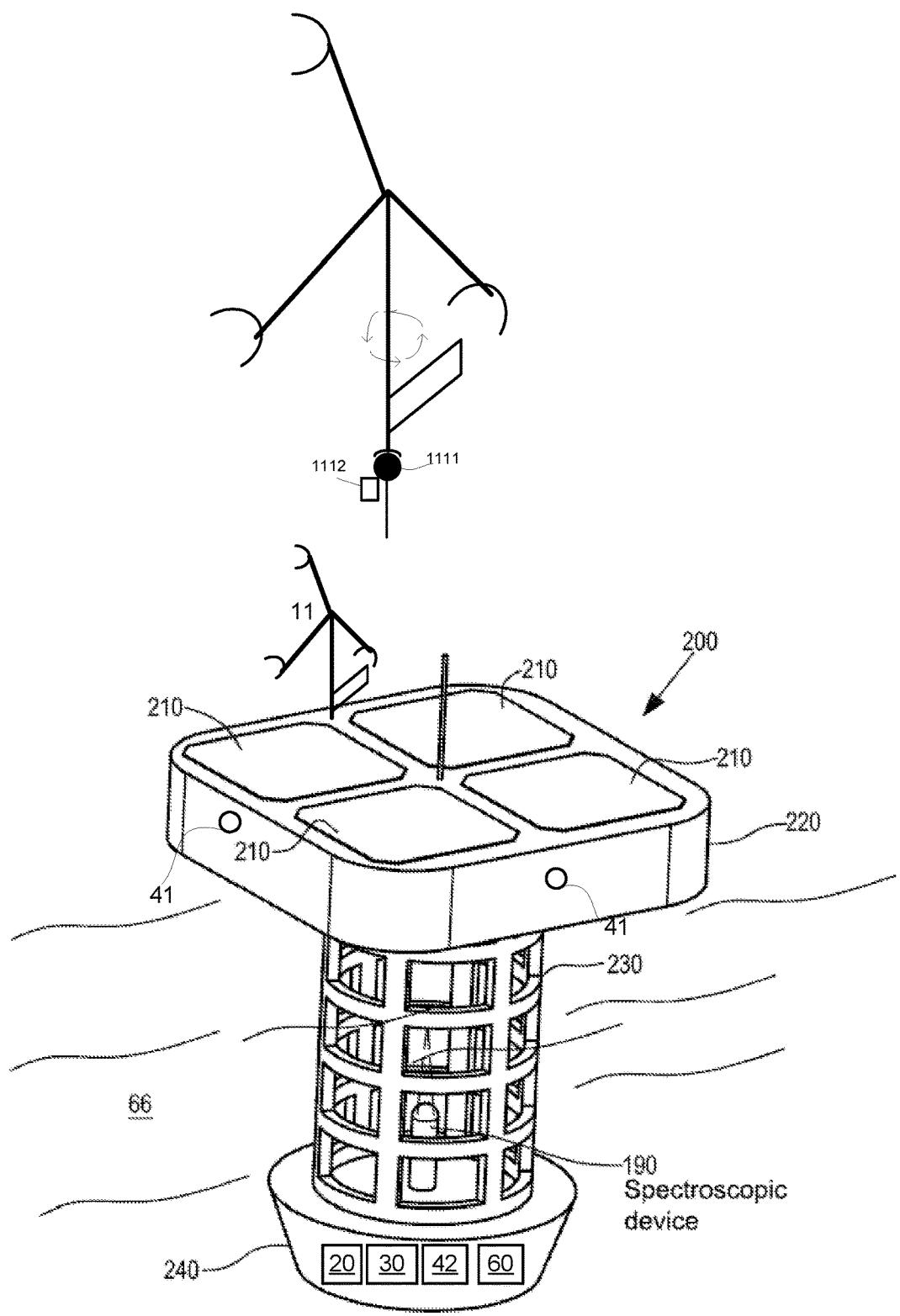
FIG. 2 is an examples of a floating system.

12—housing of anemometer
20—controller
30—propulsion system
31-34—first till fourth engines and impellers
35—fluid distributor of jet propulsion system
36—fluid conduits of jet propulsion system
41—top sensors
42—bottom sensors
43—accelerometer
44—spectroscopic camera
45—compass
51—charging plates
52—rechargeable battery
53—external pins
60—communication module
61—antenna
66—fluid
111—anemometer
112—top of housing of anemometer
113—apertures in top of housing
114—lower part of housing of anemometer (supporting element)
120—anemometer
121—fins of anemometer
122—housing that surrounds the fins
123—support element
124—axis of rotation of the fins
125—supporting elements of housing.
190—spectroscopic device
200—floating system
210—photovoltaic cell
220—floating unit
230—grid
240—bottom.
241—additional housing It should be noted that any of the components of the floating system may be positioned in any location, and that the amount of each component may be differ from those illustrated in the figures. For example, while FIG. 2 illustrated two top sensors—the number of top sensors may differ than two (for example two other top sensors may be positioned in the two other facets of floating unit that are not shown in FIG. 2. Yet for another example—the number of motors and/or jet exit points may differ from 3 or 4.

Any combination of any of the components illustrated in any of the figures and/or the specification may be provided.

It should be noted that the spectroscopic device 190 may be located within another housing that differs from grid 230, that the housing of the spectroscopic device may include or may be connected to one or more sensors and/or one or more propulsion elements, and the like.

Any components that is illustrated in bottom 240 may be located in additional housing 241 or in any other location.

Referring to FIGS. 1-9—floating system 200 (or "the float" or "Float") includes a submerged unit that includes grid 230 and a bottom 240. The grid 230 and the bottom 240 are submerged when the system 200 is placed in a pool. The floating unit 220 may include photovoltaic cells 210 (arranged in one or more panels) for supplying power to system 200. Additionally or alternatively, system 200 may include a battery or any other power supply and a control PCB.

It is further noted that part of the grid 230 may be above the fluid level and include a PCB communications antenna System 200 may be a floating system that floats freely in the pool (a free floating system) or it may move into an active motorized propulsion mode while still free floating; and may contain an onboard chemical compound dispenser facility such as a flocculant (not shown).

System 200 may further include floats and ballasting weights to keep the system floating normal at and in relation to the water surface. Solar panels to power on board control and wireless communications pack comprising a communication antenna being able to wirelessly communicate via or through the floating unit 220.

The propulsion system may include an electrical mini-pump with jet thrusting capabilities through jet nozzles in the body of the float.

Alternatively, a small propeller or propellers may be located inside the bottom 240 so that users may not get hurt if and when coming in contact with the rotating propeller (not shown).

There may be be provided a generator that may convert mechanical movement of the propulsion system to electricity and then power other electronic components or sensors on board the floating system such as sensors or a control box The propulsion system may be powered by batteries or rechargeable batteries.

The floating system may include charging pins whereby the entire floating system may be taken out of the pool and placed on a platform for charging when out of the swimming pool (not shown). The floating system may be charged using contact or contactless techniques—for example charging plates 51 may be external or internal—and may be used for contact or contactless charging.

Alternatively or additional the charging platform may be an external inductive charging platform (not shown) whereby the inductive charging surface is located underneath the bottom 240 that also contains the battery compartment, motor, pump, control and the like. Bottom 240 may be removed by unscrewing and detaching it from grid 230.

The inductive charging platform may alternatively be located inside the pool. For example, anywhere on the walls of the pool where the platform can be powered by an external power supply. This embodiment provides for an automatic battery recharging function on a docking station whereby, by means of sensors, the floating system recognizes the location of the docking station. As soon as the floating system reaches the inductive charging docking station, the floating system may remain attached to the charger by means of for example, a magnet system that may be located on an arm or arms that protrude outwards.

The floating system may include one or more sensors for sensing a status of the float.

A status of the floating system may be fed to a computerized control box or a controller that may be configured to control a movement of the floating system based on a status of the floating system as sensed by the one or more sensors and based on one or more scheduled analysis of the fluid of the pool by the water analysis device or devices.

The status of the floating system may be selected out of a speed of propagation of the float, an inclination of float, an acceleration of the float, and vibrations of the floating system and the like.

The floating system may include a simultaneous localization and mapping (SLAM) navigation system that includes some or all of an accelerometer, tilt sensor, acoustic transducers or a camera or another type of optical device such as a range finding laser that will allow the floating system to triangulate its location in relation to pool walls or any other pool structures.

With the aforesaid sensors, such as gyrocompass and accelerometer, the float's directional drift or sudden drift and speeds of said drifts from routine, pre-programmed water surface trajectory or scanning, may be identified and analyzed for corrective action by the float's controls.

The floating system may therefore further, or alternatively, include an anemometer or a wind sensor device that can measure the force of an airflow or wind flow and/or the direction of said airflow so that if the floating system starts to drift due to a gush or prolonged gushes of wind, the floating system may recognize that it may be drifting abnormally and/or becomes trapped in a certain area of the pool due to some irregular external causes such as wind factor.

Wind sensor, anemometers or air velocity or wind direction devices can be inexpensive and miniaturized produced by such as accel Controls PVT. Ltd, Mumbai, India or purchased through Amazon from Tacklife, USA and the like. Such anemometer may include rotating wind cups and a wind direction tail or be constructed of a small rotating wind or airflow cylinder containing wind direction and/or wind power sensors whereby the signals may be converted digitally so that they may be processed by the on-board PCB control box processor.

The Control box PCB may also comprise of memory capacity to memorize the shapes, sizes and location of pool boundaries (such as walls or a beach entry section) so that upon restarting of a new water surface scanning it may plot its planned trajectory and the cycle of liquid sampling.

Importantly, the gushes of wind may fill the pool with debris; it may also disturb and shift substantial quantities of surface water to at least one side of a pool thereby concentrating debris and/or water chemicals in one section of the pool that may provide wrong analysis of pool water.

The debris may include organic elements (such as leaves) which interact with chlorine and thus reduces the concentration of the chlorine at their vicinity—or otherwise bias or contaminate the fluid analysis.

Accordingly—the floating system (for example th controller) may perform at least one out of:

a. Determine to delay the fluid analysis till the end of a windy period (during at least a majority of the period the wind impact exceeds a threshold).
b. Determine to delay the fluid analysis till after a certain delay after the end of a windy period.
c. Determine to analyze fluid at an analysis point away from the debris.
d. Determine to analyze fluid at an analysis point at a region of the pool that is positioned at an opposite direction (or a substantially opposite direction) to the direction of the wind.
e. Determine an analysis point outside a region of the pool that is suspected as including the debris, and the like.

The mentioned above wind related determining of the analysis point and/or timing of the fluid analysis may increase the reliability of the fluid analysis and overcome wind induced problems.

Further, the floating system may be a battery powered and a motorized device that may travel against the wind gushes (or against the stream) to other pool locations even if being restricted by wind to a side or a corner of the pool.

Nevertheless, the floating system may sense the wind speed and force (impact of the wind) and refrain from wasting battery energy trying to move out of its "entrapped" location.

Alternatively, using the anemometer or a wind sensor (with or without any additional involvement of other sensors) the wind power and angle(s) may be fed to the SLAM system so that the floating system may navigate its way out using the least battery energy consuming path.

The floating system may include at least one water analysis instrument such as PH or Chlorine measurement probes.

In a preferred embodiment, the floating system includes a spectroscopic device 190.

The spectroscopic device 190 may be removable.

The spectroscopic device 190 may analyze fluid that flows through the apertures of grid 230.

The submerged, removable, waterproof, battery operated spectroscopic device 190 may be attached to the grid 230.

The floating system may include a controller that may be configured to receive from the spectroscopic device a result of an analysis of the fluid of the pool and to schedule, based on the result, another analysis of the fluid of the pool.

The spectroscopic device 190 may act as a mass spectrometer able to recognize common pool microorganisms whereby the DNA of such microorganisms are pre-programmed into its memory chip.

Mentioned above were generally described common pool residents such as: algae, bacteria, fungi, viruses, microbes and the like but specific recognitions—by a home owner in his backyard pool—of collie family member(s) or uropathogens may provide benefits in protecting other swimmers, especially kids, and initiating immediate counter measures to bring the pool back to hygienic standards.

The floating system may include a controller that may be configured to schedule multiple analyses of the fluid of the pool at different locations within the pool.

The at least two locations of the different locations may be positioned at different distances on the surface of the pool.

Such said multiple analyses are of importance in the event of some anomalies occurring such as the said wind or waves effects.

The floating system may include additional emergency photovoltaic solar panels if the batteries go flat or if—within the context of an embodiment that does not provide for an automatic recharging platform inside the pool area—the end user forgets to recharge the floating system or the floats' batteries.

FIG. 1 illustrates floating system 200 that includes photovoltaic cells 210, floating unit 220, grid 230, bottom 240, spectroscopic device 190, anemometer 11 (including a wide direction sensing tail), controller 20, propulsion system 30, bottom sensors 42, and communication module 60 and antenna 61.

Bottom sensors are sensors located at the bottom of the system while top sensors are sensors that are located at the top. These sensors may be any type of sensors including any of the mentioned above sensors.

FIG. 2 differs from FIG. 1 by illustrating top sensors 41. FIG. 2 also illustrates that the anemometer 11 may include a bearing 1111 (or other rotation enabling mechanism) that allows the upper part of the anemometer to rotate (in relation to the lower part of the anemometer) and also a rotation sensor 1112 for sensing the rotation. The rotation is wind induced and may provide an indication about the speed of the wind.

Figure 3:
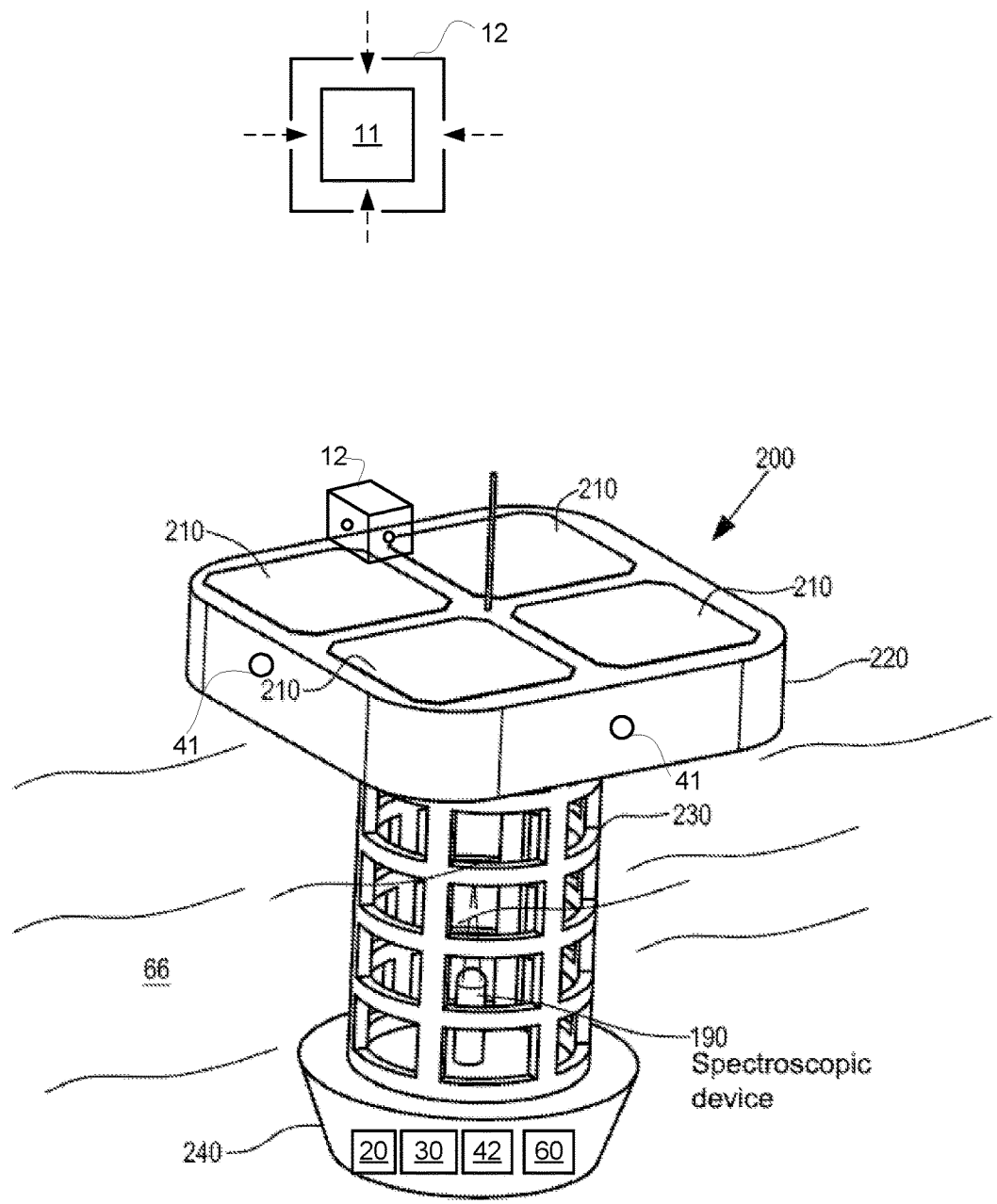
FIG. 3 is an examples of a floating system.

FIG. 3 differs from FIG. 1 by illustrating top sensors 41 and by including a housing 12 that surrounds anemometer 110 and feeds the anemometer with wind from four directions (see the top cross sectional view at the upper part of FIG. 3). The internal housing 12 may comprise waterproofed pressure sensors able to measure the force of wind applied.

Figure 4:
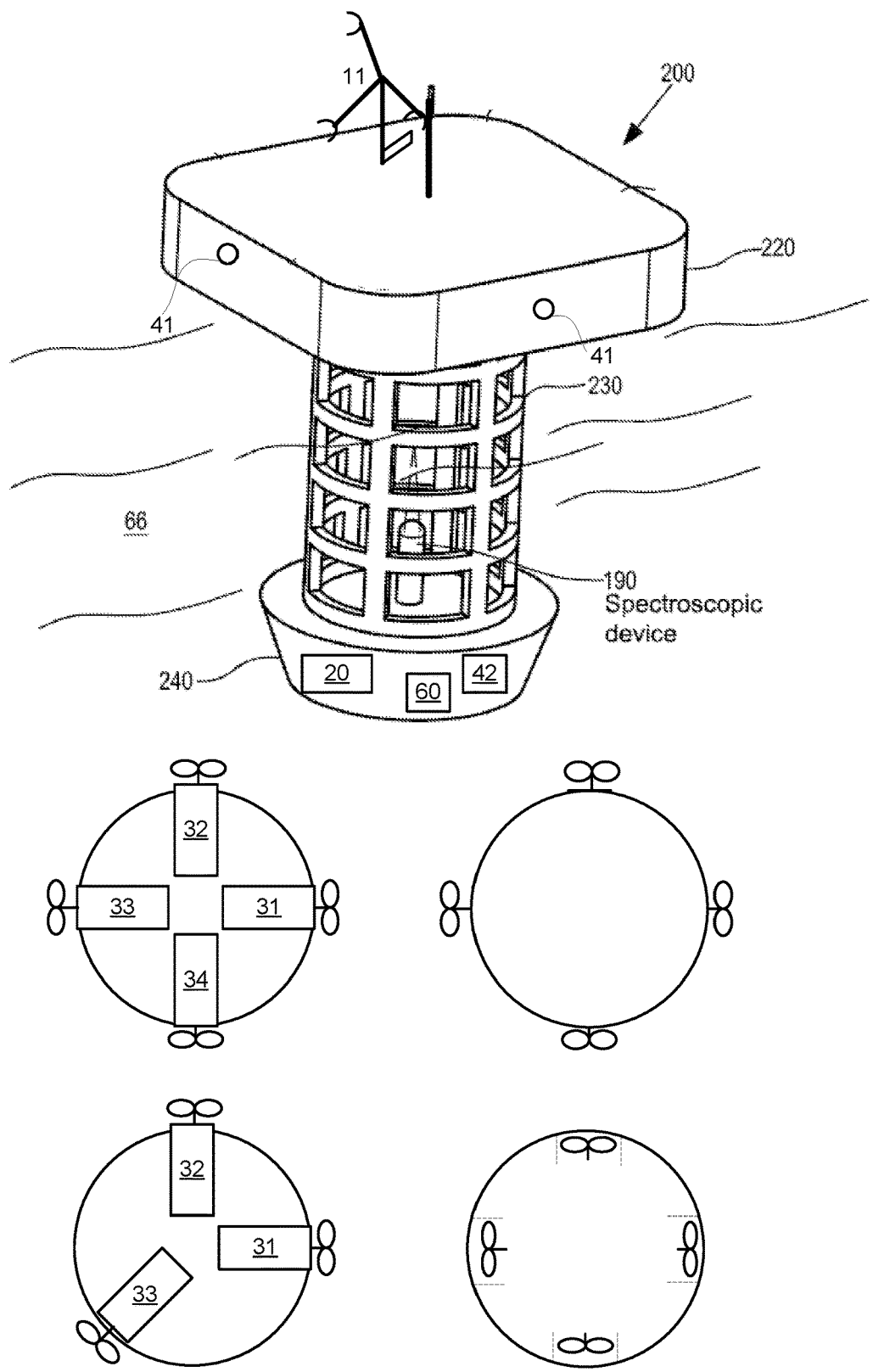
FIG. 4 is an examples of a floating system.

FIG. 4 differs from FIG. 1 by not including any photovoltaic cells 210, and by illustrating (instead of box 30) four (or three) motors and impellers 31, 32, 33 and 34 of the propulsion system. The motors may be positioned below bottom, only the impellers may extend outside the perimeter of the bottom—or the motors and the impellers may be located inside the housing—within interior spaces (such as tunnels).

Figure 5:
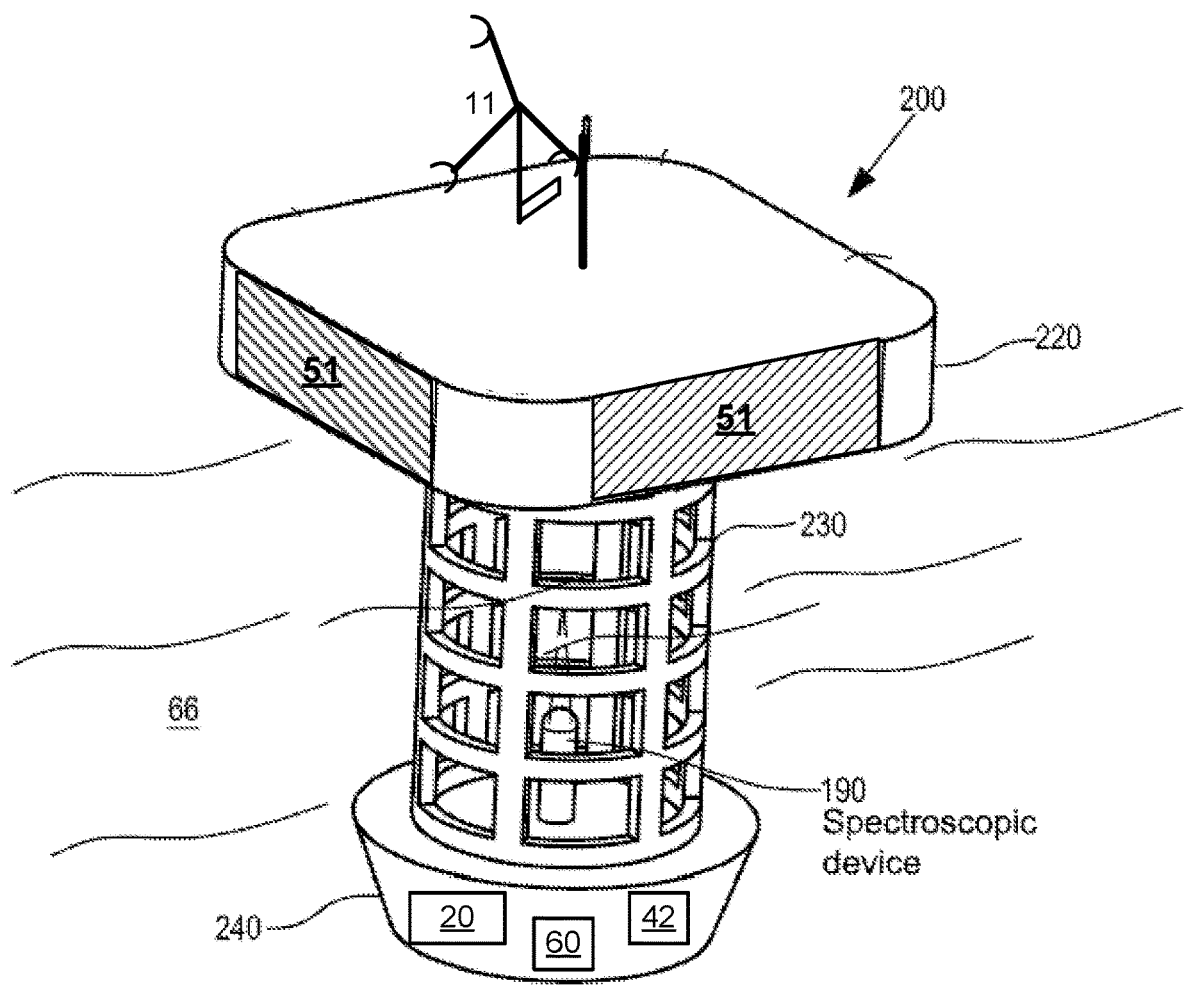
FIG. 5 is an examples of a floating system.
Figure 5:
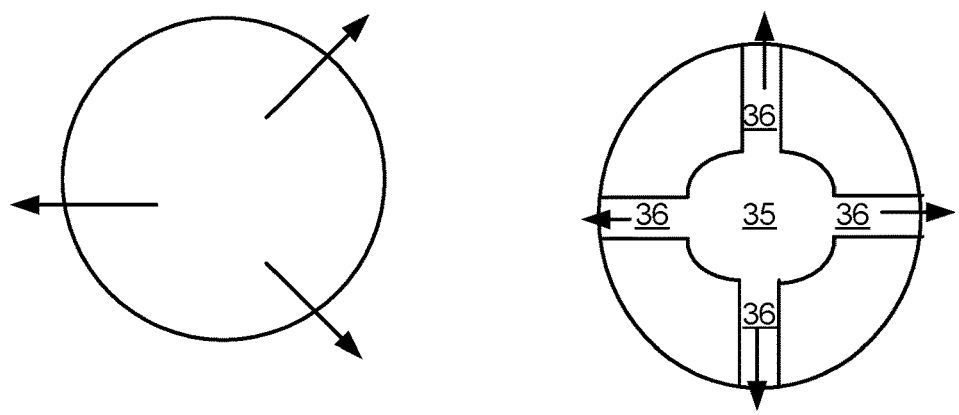

FIG. 5 differs from FIG. 1 by not including any photovoltaic cells 210, by including charging plates 51 and by illustrating (instead of box 30) four (or three) jet propulsion streams—and also by showing fluid distributor 35 of a jet propulsion system, and fluid conduits 35 of 5 the jet propulsion system.

Figure 6:
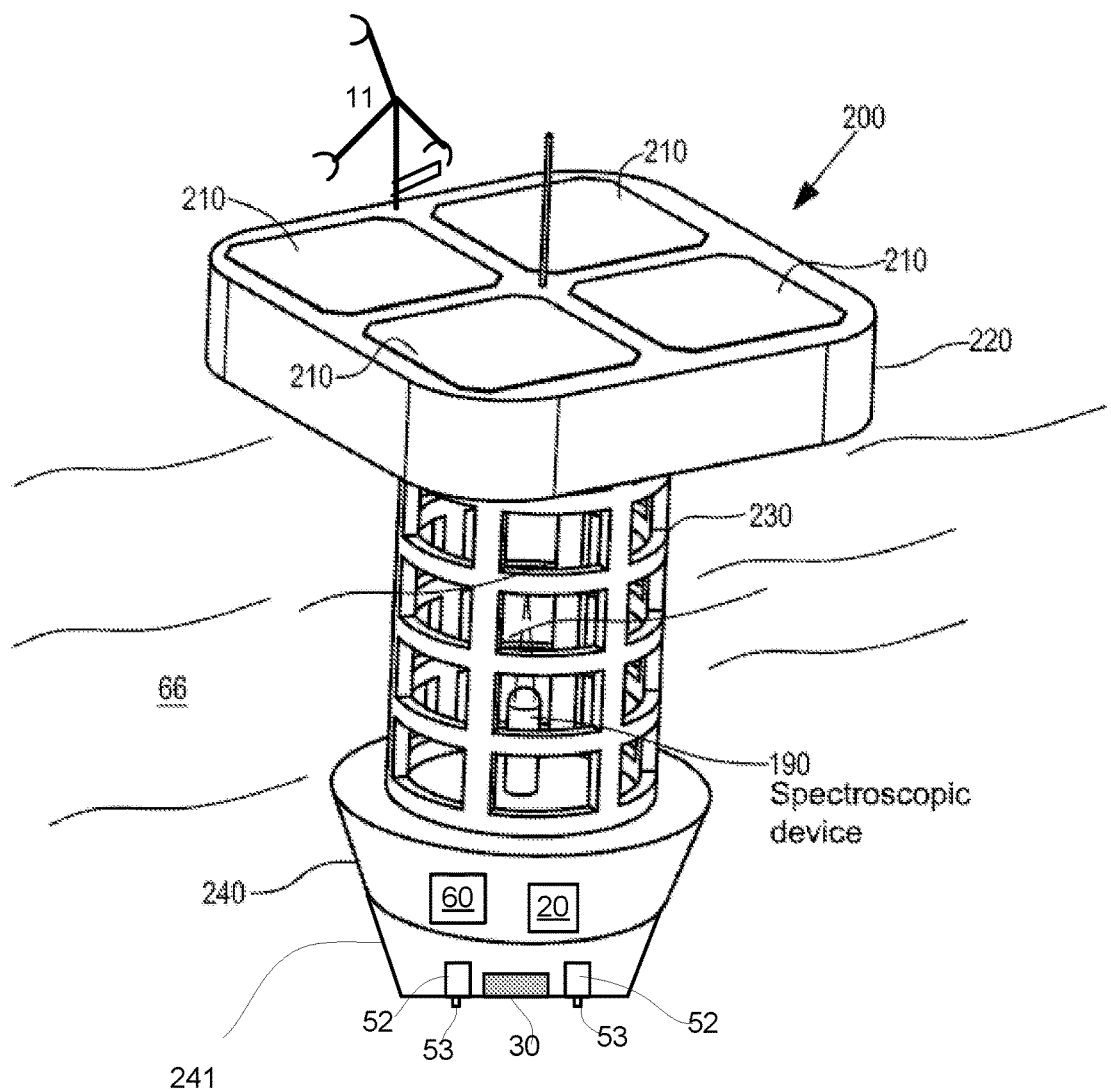
FIG. 6 is an examples of a floating system.
Figure 6:
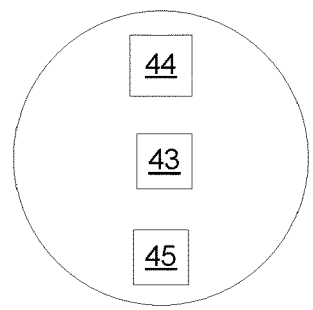

FIG. 6 differs from FIG. 1 by including additional housing 241 that may enclose rechargeable batteries 56, propulsion system 30. The rechargeable batteries 56 are electrically coupled to external pins 53 that extend outside the additional housing 241. FIG. 6 also shows some bottom sensors such as accelerometer 43, spectroscopic camera 44 and compass 45—although any combination of any sensors may be provided.

Figure 7:
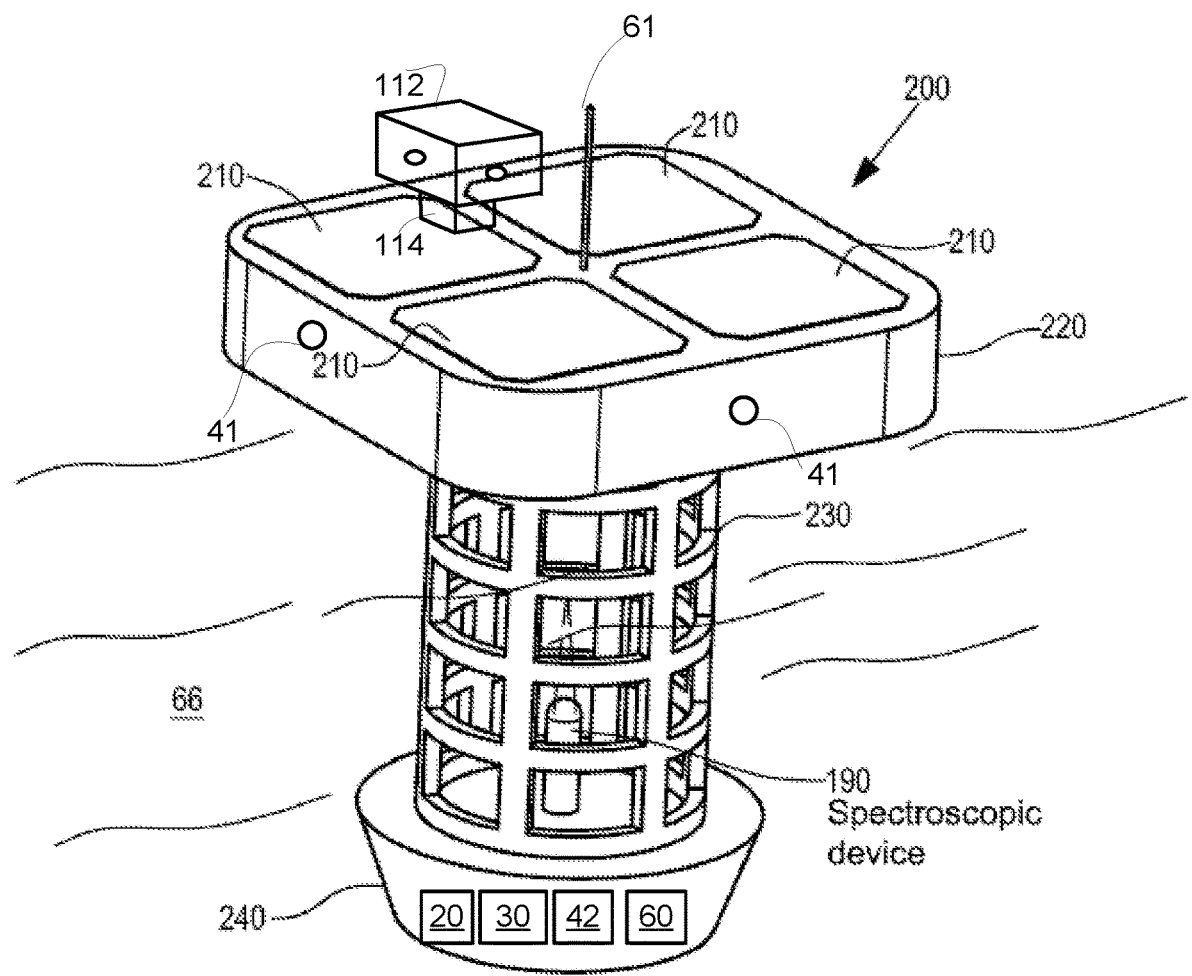
FIG. 7 is an examples of a floating system.

FIG. 7 differs from FIG. 3 by having a T-shaped housing for the anemometer—a top 112 of the housing that surrounds the anemometer and is supported by the lower part 114 of housing. The internal housing 112 may include waterproofed pressure sensors able to measure the force of wind applied when penetrating the hollow housing.

The lower part of the housing 114 supports and elevates the top part of housing. Further, the perpendicular axis leg of 114 may rotate 720 degrees and so pivoting the entire structure of 112 around the said axis. The leg may be connected anywhere to the housing 220 where is not submerged underwater by means of a ball bearing located in a sealed ball bearing housing (not shown). The pivoting of the 112 provides the wind direction. The pressure sensor provides the wind force but, in another embodiment, both functions may be combined.

Figure 8:
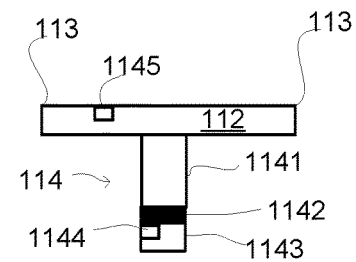
FIG. 8 is an examples of a floating system.
Figure 8:
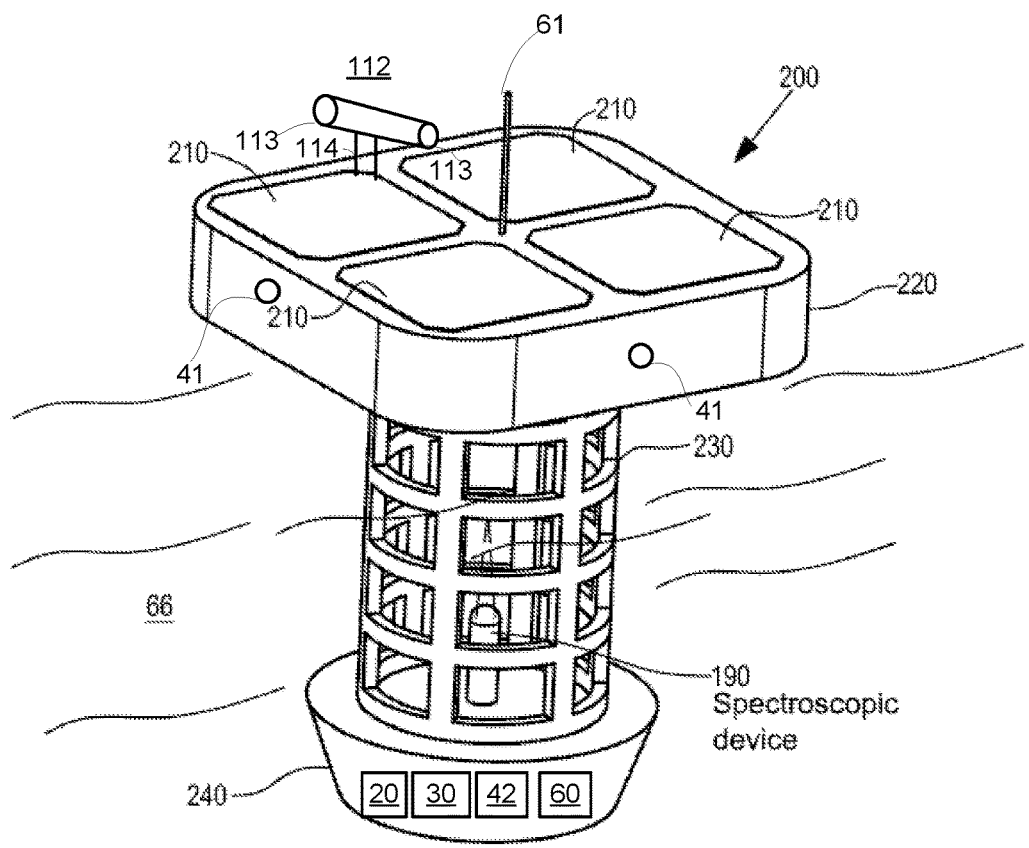

FIG. 8 differs from FIG. 3 by having a T-shaped anemometer 111, that has a pipe 112 with two openings 113 and one or more sensors 1145 installed within the pipe 112, a base 114 that includes an upper part 1141 that rotates with the pipe (according to the direction of the wind), a bearing 1142 bearing 1111 (or other rotation enabling mechanism) that allows the upper part of the anemometer to rotate (in relation to the lower part 1143 of the anemometer) and also a rotation sensor 1144 for sensing the rotation. The rotation is wind induced and may provide an indication about the speed of the wind.

Figure 9:
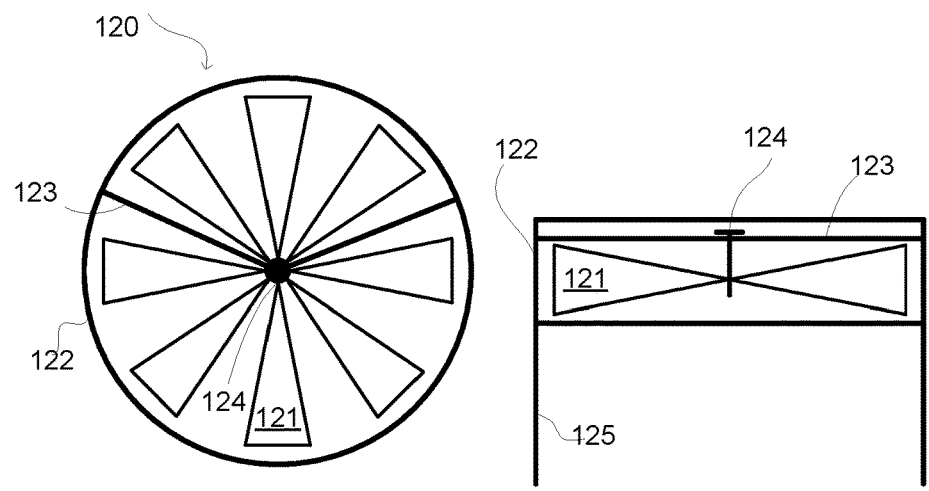
FIG. 9 is an examples of a floating system.
Figure 9:
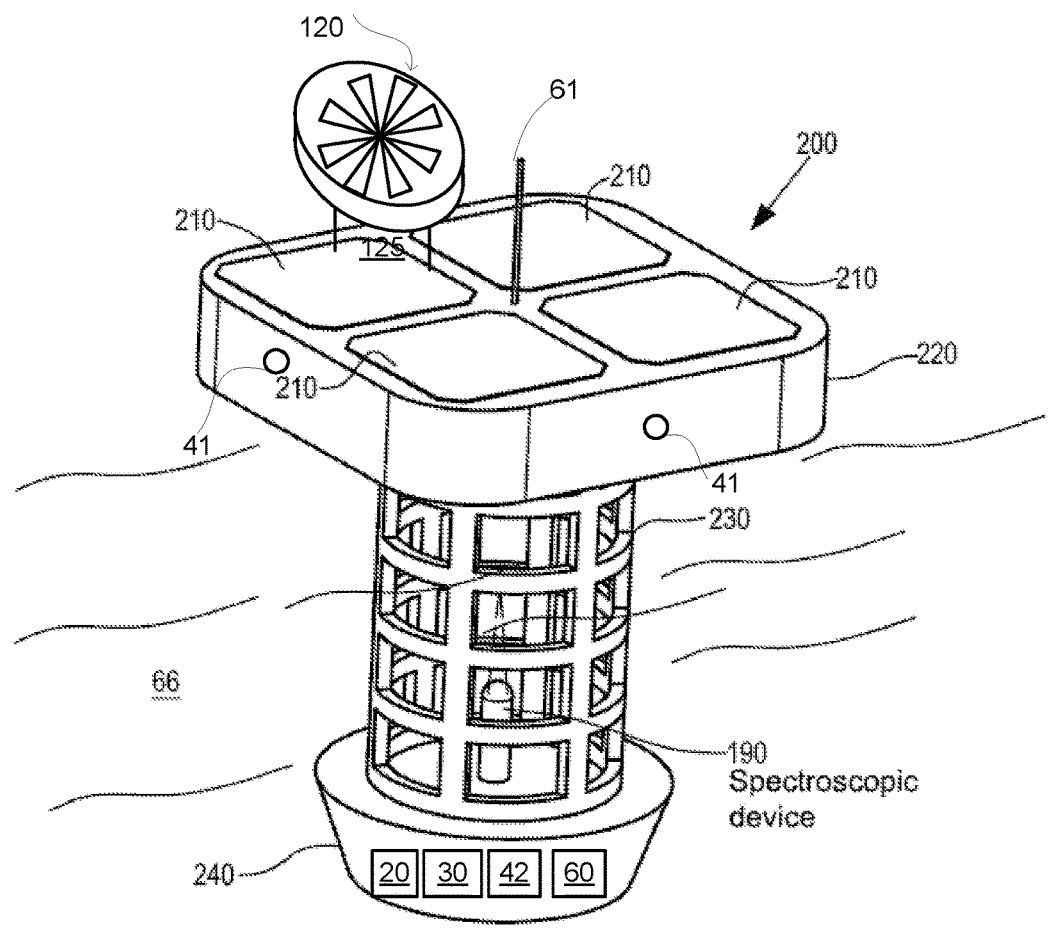

FIG. 9 differs from FIG. 3 by having a cylindrical anemometer 121 that include a housing 122 that may be hollow and have a cylindrical interior (or other shaped interior) 122 that surrounds the fins 121 of the anemometer. The fins 121 may be rotated by the wind and turn around an axis 124. The axis may be mechanically coupled to the housing 122 via support elements 123.

The housing 122 may be supported by support elements 125 such as legs.

Figure 10:
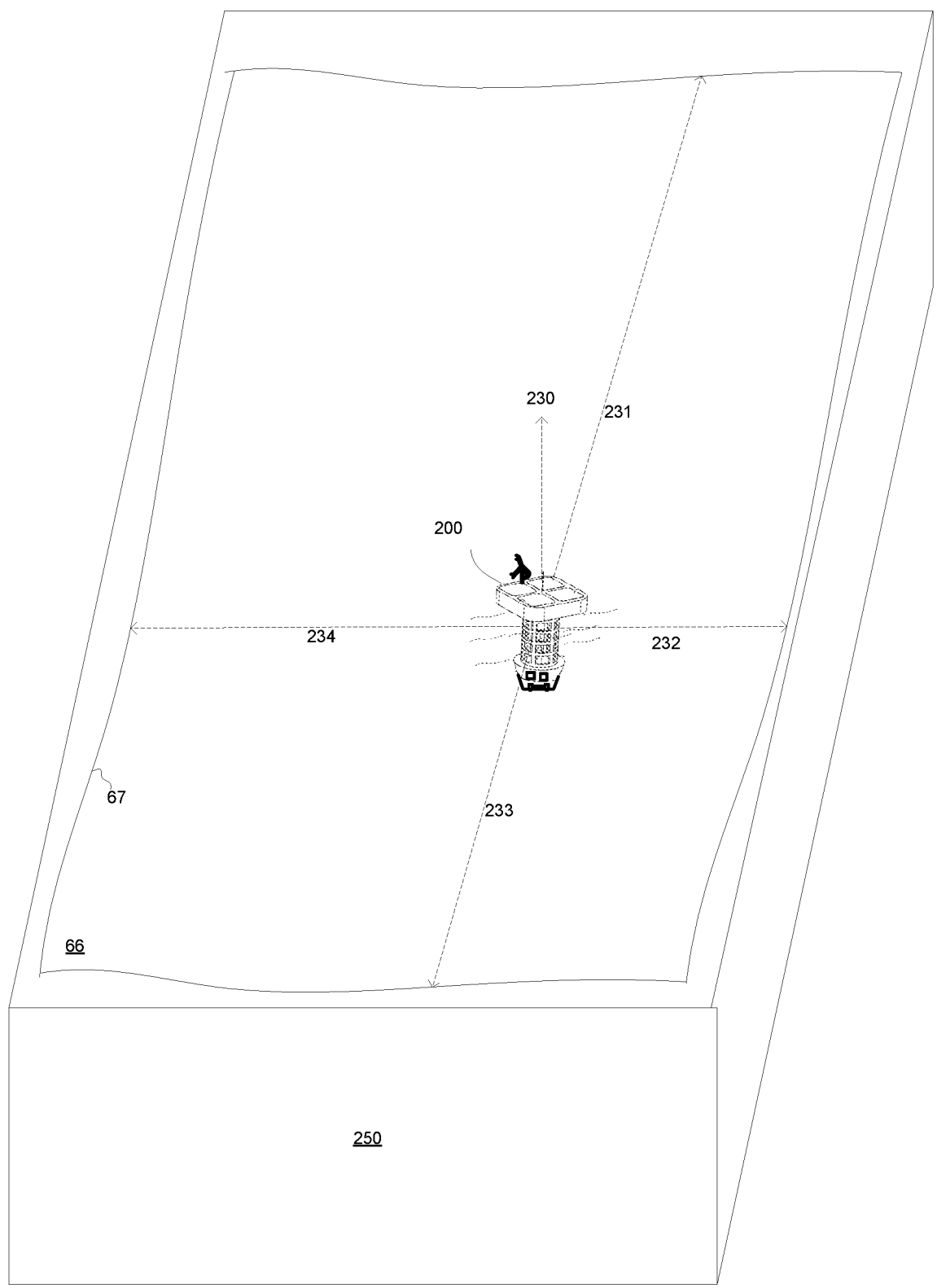
FIG. 10 is an examples of a floating system and a pool.

FIG. 10 illustrates the floating system 200 and also the orientation 230 of the floating system and distances (231, 232, 233 and 234) between the floating system and the sidewalls of a pool 250. Fluid 66 is also illustrated and so is the waterline 67.

Figure 11:
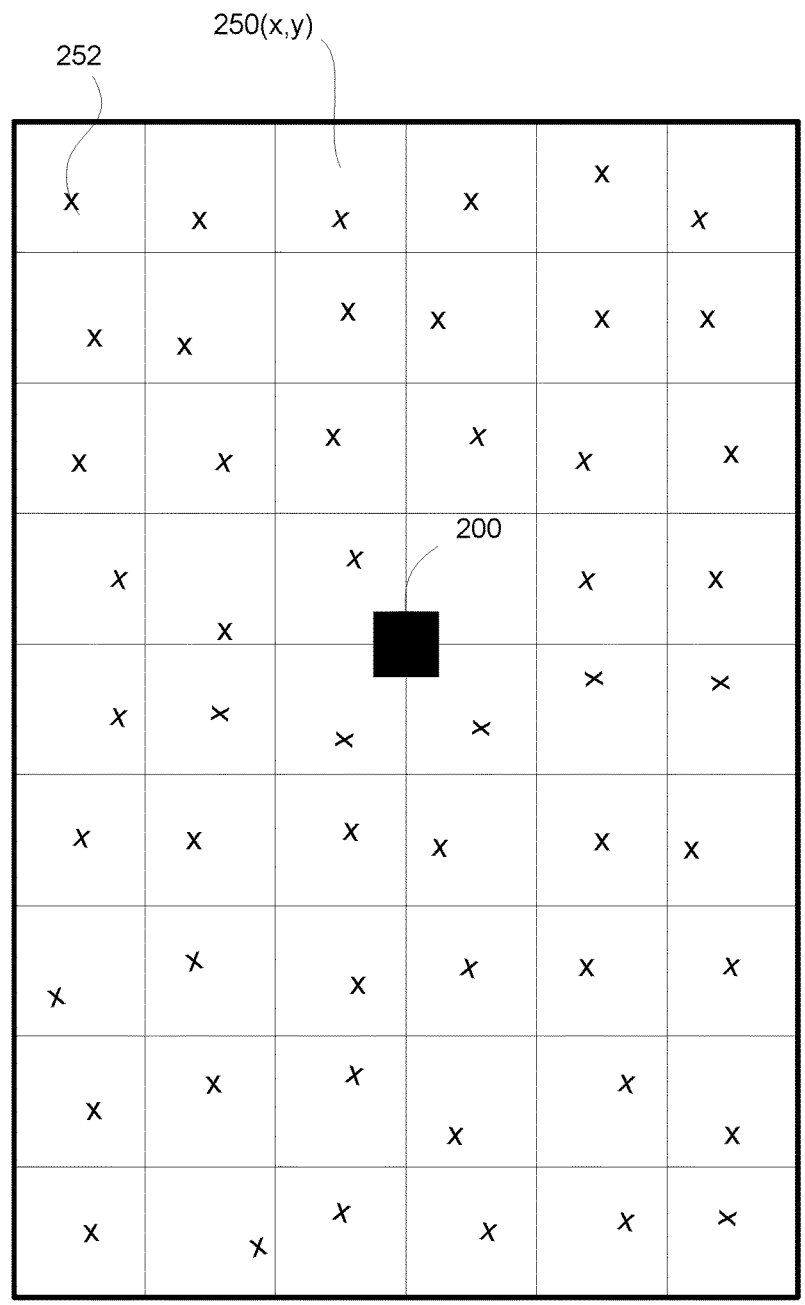
FIG. 11 is an examples of a floating system and a pool.
Figure 12:
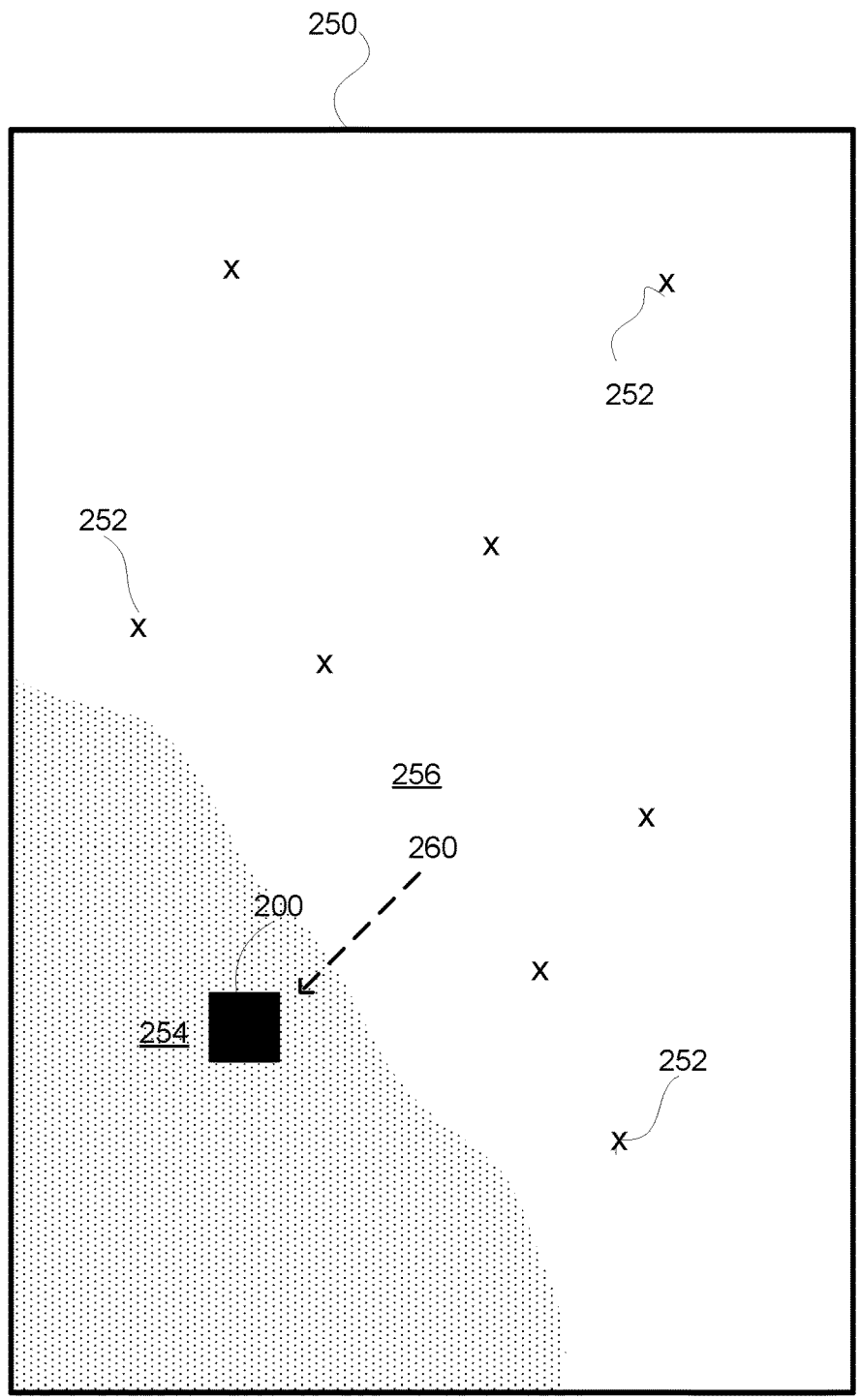
FIG. 12 is an examples of a floating system and a pool.

FIG. 11 illustrates a pool 250 that is virtually segmented to multiple segments 250(x,y) and multiple analysis points—one per segment. It should be noted that the shape, size and number of the segments may differ from those illustrated in the figure, that the number of analysis points per segments may differ from one, that the number of analysis points per one segment may differ from the number of analysis points in another segments, that the locations of the analysis points may change over time, may depend on wind and/or results of fluid analysis, that the floating system may apply any analysis scheme and that the timing of analysis and location of the analysis points may be determined in any manner FIG. 12 illustrates a pool 250, a wind direction 260, a region 254 impacted by the wind (includes debris) and a region 256 not impacted by the wind (does not include debris or sparse floating debris). One or more analysis points 252 may be defined within each region. Thus—defining one or more additional analysis points 252 within region 246 may improve the quality of fluid analysis.

Figure 13:
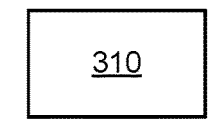
FIG. 13 is an examples of a method.
Figure 13:
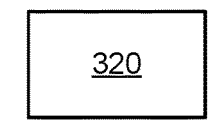
Figure 13:
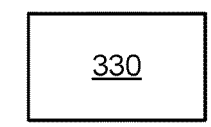
Figure 13:
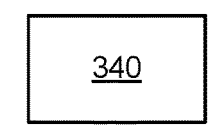
Figure 13:
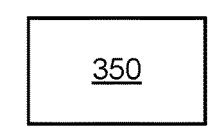

FIG. 13 illustrates method 300 according to an embodiment of the invention.

Method 300 is for analyzing a fluid of a pool by a floating system.

Method may include steps 310, 320, 330 and 340.

Step 310 may include sensing, by a sensor of the floating system, at least one out of (a) a wind parameter related to a wind that impinges on the floating system and (b) a movement of the floating system. The sensor belongs to a floating system that may also include a top portion comprises at least one float, a submerged portion that comprises comprises a fluid analysis instrument, a power source, a controller, and a propulsion unit.

Step 320 may include determining, by the controller, an impact of the wind on the floating system based on the at least one out of the wind parameter and the movement of the floating system.

Step 330 may include controlling, by the controller, a movement of the floating system based, at least in part, on the impact of the wind.

Step 340 may include analyzing, by the fluid analysis instrument, at one or more analysis points, the fluid of the pool to provide one or more fluid analysis results.

The method may include step 350 of determining at least one analysis parameter. The analysis parameter may be the location of the one or more analysis points and/or the timing of the analysis. The movement of the floating system may move the floating system between one analysis point to another.

The analysis parameter may be defined in any manner—following any analysis rules related to the location and/or timing of the fluid analysis.

The determining of step 350 may be based, at least on part, on the impact of the wind. The controller may determine at least one analysis point and/or nay receive from another party the location of at least one analysis point.

Step 320 may include determining a direction of the wind. Step 350 may include determining an analysis point to be at an location that is positioned, in relation to a location of the floating system, at an direction that is opposite to the direction of the wind. For example—analysis point within region 256 of FIG. 12.

The determining of step 350 may be based, at least on part, on an analysis result. For example—if the analysis is indicative of a potential problem then the frequency of analysis may be increased in relation to the frequency of analysis following an analysis that is indicative of a proper fluid content.

Step 330 may include stopping a movement of the floating system by the propulsion unit when an impact of the wind exceeds an impact threshold. This may save power—especially during gushes of wind.

Step 350 may include scheduling, by the controller, a timing of an analysis of the fluid based, at least in part, on the impact of the wind and on the analysis result.

Step 350 may include determining, by the controller, a timing of an analysis of the fluid based and an analysis point of the analysis based, at least in part, on the impact of the wind and on the analysis result.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Any reference to any of the terms "comprise", "comprises", "comprising" "including", "may include" and "includes" may be applied to any of the terms "consists", "consisting", "consisting essentially of". For example—any of the circuits illustrated in any figure may include more components that those illustrated in the figure, only the components illustrated in the figure or substantially only the components illustrate din the figure.

Also for example, in one embodiment, the illustrated examples may be implemented as circuitry located on a single integrated circuit. Alternatively, the examples may be implemented as any number of separate integrated circuits or separate common mode noise chokes interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

Unless stated otherwise, terms such as "first" and "second" are used to arbitrarily distinguish between the elements such terms describe. Thus, these terms are not necessarily intended to indicate temporal or other prioritization of such elements The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for analyzing a fluid of a pool by a floating system, the method comprises:
    sensing, by a sensor of the floating system, at least one out of (a) a wind parameter related to a wind that impinges on the floating system and (b) a movement of the floating system; wherein the floating system further comprises a top portion that comprises at least one float, a submerged portion that comprises a fluid analysis instrument, a power source, a controller, and a propulsion system; wherein the propulsion system comprises (a) one or more motors configured to rotate one or more impellers, or (b) an pump with jet thrusting capabilities and one or more jet nozzles;
    determining, by the controller, an impact of the wind on the floating system based on the at least one out of the wind parameter and the movement of the floating system;
    controlling, by the controller, a movement of the floating system based, at least in part, on the impact of the wind; and
    analyzing, by the fluid analysis instrument, at one or more analysis points, the fluid of the pool to provide one or more fluid analysis results.

2. The method according to claim 1, wherein the sensor is an anemometer.

3. The method according to claim 1, wherein the sensor is selected out of a pressure sensor, a velocity sensor and an accelerometer.

4. The method according to claim 1, wherein the fluid analysis instrument is a spectrometer.

5. The method according to claim 1, comprising determining the one or more analysis points based on the impact of the wind.

6. The method according to claim 1, comprising determining a direction of the wind and determining an analysis point to be at an location that is positioned, in relation to a location of the floating system, at an direction that is opposite to the direction of the wind.

7. The method according to claim 1 wherein the controlling of the movement of the floating system comprises stopping a movement of the floating system by the propulsion system when an impact of the wind exceeds an impact threshold.

8. The method according to claim 1 comprising determining, by the controller, a timing of an analysis of the fluid based, at least in part, on the impact of the wind.

9. The method according to claim 1 comprising receiving by the controller an analysis result of the fluid and scheduling, by the controller, a timing of an analysis of the fluid based, at least in part, on the impact of the wind and on the analysis result.

10. The method according to claim 1 comprising receiving by the controller an analysis result of the fluid and determining, by the controller, a timing of an analysis of the fluid based and an analysis point of the analysis based, at least in part, on the impact of the wind and on the analysis result.

11. A floating system comprising:
   a top portion:
   a submerged portion;
   a sensor;
   a processor;
   a propulsion system that is configured to move the floating system; wherein the propulsion system comprises (a) one or more motors configured to rotate one or more impellers, or (b) an pump with jet thrusting capabilities and one or more jet nozzles;
   wherein the top portion comprises at least one float;
   wherein the submerged portion comprises a fluid analysis instrument that is constructed and arranged to analyze a fluid, at one or more analysis points;
   wherein the sensor is constructed and arranged to sense at least one out of (a) a wind parameter related to a wind that impinges on the floating system and (b) a movement of the floating system;
   wherein the processor is constructed and arranged to (i) determine an impact of the wind on the floating system based on the at least one out of the wind parameter and the movement of the floating system, and (ii) control the propulsion system based, at least in part, on the impact of the wind.

12. The floating system according to claim 11, wherein the sensor is an anemometer.

13. The floating system according to claim 11, wherein the sensor is selected out of a velocity sensor and an accelerometer.

14. The floating system according to claim 11, wherein the fluid analysis instrument is a spectrometer.

15. The floating system according to claim 11, wherein the controller is constructed and arranged to determine the one or more analysis points based on the impact of the wind.

16. The floating system according to claim 11, wherein the controller is constructed and arranged to determine a direction of the wind and determine an analysis point to be at an location that is positioned, in relation to a location of the floating system, at an direction that is opposite to the direction of the wind.

17. The floating system according to claim 11 wherein the controller is constructed and arranged to stop a movement of the floating system by the propulsion system when an impact of the wind exceeds an impact threshold.

18. The floating system according to claim 11 wherein the controller is constructed and arranged to determine a timing of an analysis of the fluid based, at least in part, on the impact of the wind.

19. The floating system according to claim 11 wherein the controller is constructed and arranged to receive an analysis result of the fluid and schedule a timing of an analysis of the fluid based, at least in part, on the impact of the wind and on the analysis result.

20. The floating system according to claim 11 wherein the controller is constructed and arranged to receive an analysis result of the fluid and determine a timing of an analysis of the fluid based and an analysis point of the analysis based, at least in part, on the impact of the wind and on the analysis result.

* * * * *